(12) United States Patent
Mahmud et al.

(10) Patent No.: US 8,097,343 B2
(45) Date of Patent: Jan. 17, 2012

(54) FUNCTIONALIZED DENDRITIC POLYMERS FOR THE CAPTURE AND NEUTRALIZATION OF BIOLOGICAL AND CHEMICAL AGENTS

(75) Inventors: Khaled Mahmud, Sudbury, MA (US); Lawino Kagumba, Cambridge, MA (US); Franciscus Johannes Marie Derks, Heythuysen (NL)

(73) Assignees: Triton Systems, Inc., Chelmsford, MA (US); DSM IP Assets B.V. (NL)

( * ) Notice: Subject to any disclaimer, the term of this patent is extended or adjusted under 35 U.S.C. 154(b) by 479 days.

(21) Appl. No.: 11/423,580

(22) Filed: Jun. 12, 2006

(65) Prior Publication Data

US 2007/0071713 A1 Mar. 29, 2007

Related U.S. Application Data

(63) Continuation-in-part of application No. 11/216,728, filed on Aug. 31, 2005, now Pat. No. 7,384,626.

(60) Provisional application No. 60/606,077, filed on Aug. 31, 2004.

(51) Int. Cl.
*A61K 31/74* (2006.01)
*A61K 47/48* (2006.01)
*A61K 33/02* (2006.01)
*C07C 211/62* (2006.01)

(52) U.S. Cl. ............ 428/446; 424/78.17; 424/78.3; 424/78.36; 424/405; 424/486; 424/DIG. 16; 428/457; 428/458; 428/474.4; 428/480; 523/205; 523/209; 523/212; 523/214; 525/326.5; 525/326.7; 525/327.3; 525/328.2; 525/329.1; 525/374; 525/375; 525/420; 525/424; 525/425; 525/434

(58) Field of Classification Search .......... 525/326.5, 525/326.7, 327.3, 328.2, 329.1, 374, 375, 525/420, 424, 425, 434; 523/205, 209, 212, 523/214; 428/446, 457, 458, 474.4, 480; 424/78.17, 78.3, 78.36, 405, 486, 719, DIG. 16
See application file for complete search history.

(56) References Cited

U.S. PATENT DOCUMENTS

| | | | |
|---|---|---|---|
| 5,490,983 A | 2/1996 | Worley et al. | |
| 5,902,818 A | 5/1999 | Worley et al. | |
| 6,045,820 A | 4/2000 | Messier | |
| 6,224,655 B1 | 5/2001 | Messier | |
| 6,245,820 B1 | 6/2001 | Kojima et al. | |
| 6,440,405 B1 | 8/2002 | Cooper et al. | |
| 6,469,177 B1 | 10/2002 | Worley et al. | |
| 6,548,054 B2 | 4/2003 | Worley et al. | |
| 6,562,885 B1 | 5/2003 | Moorehead et al. | |
| 6,592,861 B2 | 7/2003 | Messier | |
| 6,653,519 B2 | 11/2003 | Koper et al. | |
| 6,680,050 B1 | 1/2004 | Messier | |
| 6,696,055 B2 | 2/2004 | Messier | |
| 6,727,400 B2 | 4/2004 | Messier et al. | |
| 2004/0063828 A1* | 4/2004 | Loen et al. | 524/186 |
| 2004/0127667 A1 | 7/2004 | Worley et al. | |
| 2007/0202071 A1* | 8/2007 | Morvan et al. | 424/70.17 |

FOREIGN PATENT DOCUMENTS

| | | | |
|---|---|---|---|
| WO | WO 01/77270 | * | 10/2001 |
| WO | WO 2005/032497 | * | 4/2005 |

OTHER PUBLICATIONS

Tang et al., 1996, In Vitro Gene Delivery by Degraded Polyamidoamine Dendrimers, Bioconjugate Chem. 7:703-714.
Kukowska-Latallo et al., Efficient transfer of genetic material into mammalian cells using Starburst polyamidoamine dendrimers, 1996, Proc. Natl. Acad. Sci. USA 93:4897-4902.
Zeng; Dendrimers in Supramolecular Chemistry: From Molecular Recognition to Self-Assembly, 1997, S.C. Chem. Rev. 97:1681-1712.
Newkome et al., Supramolecules with Novel Properties: Metallodemdrimers, 1999, Chem. Rev. 99:1689-1746.
Liu et al., Preparation of Water-soluble Dendritic Unimolecular Micelles as Potential Drug Delivery Agents, 1999, J. Proc. Am. Chem. Soc. Polym. Mater. Sci. Engr. 80:167-168.
Uhrich, Hyperbranched Polymers for Drug Delivery, Trip 5(12):388-393.
Liu et al., Hyperbranched Polymeric Micelles Drug Encapsulation, Release and Polymer Degradation, 1997, Proc. Am. Chem. Soc. Div. Polym. Chem. 38:582-583.
Matthews et al., Dendrimers-Branching Out From Curiosities into New Technologies, 1998, Prog. Polym. Sci. 23:1-56.
Newkome et al., Dendritic Macromolecules: Concepts, Syntheses, Perspectives, VCH Publ. Weinheim, Germany, 1996 (TOC).
Newkome, 1995, Advances in Dendritic Macromolecules, JAI Press: Greenwich, Conn., vol. 2 (TOC).
Tomalia, Starburst/Cascade Dendrimers: Fundamental Building Blocks for a New Nanoscopic Chemistry Set, 1994, Adv. Mater. 6(7/8):529-539.
Tomalia et al., Communications to the Editor: Starburst Dendrimers, 4. Covalently Fixed Unimolecular Assemblages Reminiscent of Spheroidal Micelles, 1987, Macromolecules 20(5):1164-1167.
Smith, 1983, Derivatives of Hydrazine and Other Hydronitrogens Having N-N Bonds, Benjamin/Cummings Publ. Co., Canada, 18-22.
Aubort et al., Enhanced Nucleophilic Reactivity: The "Disappearing" Lone-Pair, 1973, Tet. Lett. 24:2229-2232.
Bruice et al., Aminolysis of Phenyl Acetates in Aqueous Solutions, VII: Observations on the Influence of Salts, Amine Structure and Base Strength, 1967, J. Am. Chem. Soc. 89(9):2106-2121.
Chen et al., Quaternary Ammonium Functionalized Poly(propylene imine) Dendrimers as Effective Antimicrobials: Structure-Activity Studies, 2000 Fall, Biomacromolecules 1(3):473-480.
Seiler, Dendritic Polymers-Interdisciplinary Research and Emerging Applications from Unique Structural Properties, 2002, Chem. Eng. Technol. 25:237-253.

(Continued)

*Primary Examiner* — Ana Woodward
(74) *Attorney, Agent, or Firm* — Pepper Hamilton LLP

(57) ABSTRACT

The present invention describes compositions and methods for trapping/capturing and/or destroying dangerous substances such as chemical and biological warfare agents. The present invention relates to dendritic polymers, specifically, to quaternary ammonium functionalized dendritic polymers and N-Halamine functionalized dendritic polymers. Such dendrimers are useful for the capture and neutralization of biological and chemical warfare agents.

13 Claims, 3 Drawing Sheets

OTHER PUBLICATIONS

Chen et al., Incorporation of Dimethyldodecyl-ammonium Chloride Functionalities onto Poly(propylene imine) Dendrimers Significantly Enhances Their Antibacterial Properties, 1999, Chem. Comm. 1585-1586.

Holister, Dendrimers: Technology White Papers nr. 6, Cientifica, Oct. 2003, pp. 1-15.

* cited by examiner

FUNCTIONALIZED DENDRITIC POLYMERS FOR THE CAPTURE AND NEUTRALIZATION OF BIOLOGICAL AND CHEMICAL AGENTS

CROSS REFERENCE TO RELATED APPLICATIONS

The present application is a continuation-in-part of pending U.S. patent application Ser. No. 11/216,728, filed on Aug. 31, 2005 now U.S. Pat. No. 7,384,626, which claims the benefit of and priority to U.S. Provisional Application Ser. No. 60/606,077, filed Aug. 31, 2004 the contents of which are incorporated herein by reference in their entirety.

GOVERNMENT INTEREST

The United States government may have certain rights to this invention pursuant to Grant Nos. W9132T-04-C-0007 from the United States Army and Contract No. W911SR-04-C-0098 from DARPA (Defense Advanced Research Projects Agency).

JOINT RESEARCH AGREEMENT

Not Applicable

INCORPORATION BY REFERENCE TO MATERIAL SUBMITTED ON COMPACT DISC

Not Applicable

BACKGROUND

The threat of biological and chemical warfare has grown considerably in recent times. Numerous countries are capable of developing deadly biological and chemical weapons. Some potent biological warfare agents include the following: bacteria such as *Bacillus anthracis* (anthrax) and *Yersinia pestis* (plague); viruses such as variola virus (small pox) and flaviviruses (hemorrhagic fevers); and toxins such as botulinum toxins and saxitoxin. Some potent chemical warfare agents include: blister or vesicant agents such as mustard agents; nerve agents such as methylphosphonothiolate (VX); lung damaging or choking agents such as phosgene (CG); cyanogen agents such as hydrogen cyanide; incapacitants such as 3-quinuclidinyl benzilate; riot control agents such as CS (malonitrile); smokes such as zinc chloride smokes; and some herbicides such as 2,4-D (2,4-dichlorophenoxy acetic acid).

All of the above agents, as well as numerous other biological and chemical agents, pose a significant risk to private citizens as well as to military personnel. For example, vesicant agents burn and blister the skin or any other part of the body they contact, including eyes, mucus membranes, lungs, and skin. Nerve agents are particularly toxic and are generally colorless, odorless, and readily absorbed through the lungs, eyes, skin, and intestinal track. Even a brief exposure can be fatal and death can occur in as quickly as 1 to 10 minutes. Biological agents such as anthrax are easily disseminated as aerosols and thus have the ability to inflict a large number of casualties over a wide area with minimal logistical requirements. Many biological agents are highly stable and thus can persist for long periods of time in soil or food.

There are currently two general types of decontamination methods for biological agents: chemical disinfection and physical decontamination. Chemical disinfectants, such as hypochlorite solutions, are useful but are corrosive to most metals and fabrics, as well as to human skin. Physical decontamination, on the other hand, usually involves dry heat up to 160° C. for 2 hours or steam or super-heated steam for about 20 minutes. Sometimes UV light can be used effectively, but it is difficult to develop and standardize for practical use.

These methods have many drawbacks. The use of chemical disinfectants can be harmful to personnel and equipment due to the corrosiveness and toxicity of the disinfectants. Furthermore, chemical disinfectants result in large quantities of effluent which must be disposed of in an environmentally sound manner. Physical decontamination methods are lacking because they require large expenditures of energy. Both chemical and physical methods are difficult to use directly at the contaminated site due to bulky equipment and/or large quantities of liquids which must be transported to the site. Finally, while a particular decontamination or disinfection method may be suitable for biological decontamination, it is generally not effective against chemical agents. There is a need for decontamination compounds which are effective against a wide variety of both chemical and biological agents, have low energy requirements, are easily transportable, do not harm skin or equipment and employ small amounts of liquids with minimal or no effluent. Such decontamination compounds may be useful in both military and commercial arenas such as first responders and the Heating Ventilation and Air Conditioning industry.

Because of the unique architecture of dendrimers, they have been investigated for a wide variety of applications, such as gene delivery vesicles, Tang, et al., Bioconjugate Chem., 7 at 703-714 (1996); Kukowska-Latallo, et al., Proc. Natl. Acad. Sci. USA, 93 at 4897-4902 (1996), catalysts, Zeng, F. Z., S. C. Chem. Rev., 97 at 1681 (1997); Newkome, et al., Chem. Rev., 99 at 1689-1746 (1999), drug delivery carriers, Liu, M.; Frechet, J. M., J. Proc. Am. Chem. Soc. Polym. Mater. Sci. Engr., 80 at 167 (1999); Uhrich, K., TRIP, 5 at 388-393 (1997); Liu, H.; Uhrich, K. Proc, Am. Chem. Soc. Div. Polym. Chem., 38 at 1226 (1997), chromatography stationary phases, Matthews, et al., Prog. Polym. Sci., 23 at 1-56 (1998), boron neutron capture therapy agents, Newkome, et al., Dendritic Macromolecules: Concepts, Syntheses, Perspectives; VCH: Weinheim, Germany (1996); Newkome, O. R., Advances in Dendritic Macromolecules; JAI Press. Greenwich, Conn., Vol. 2 (1995), and magnetic resonance imaging contrast agents, Tomalia, D. A. Adv. Mater., 6 at 529-539 (1994), all of which are herein incorporated by reference. Some examples of commercially available hyperbranched polymers include hyperbranched polyethylene imine (PEI) and Hybranes® (www.hybrane.com (DSM)).

Synthesized quaternary ammonium functionalized poly (propyleneimine) dendrimers have been evaluated with regard to their antibacterial properties. Bioluminescence results have confirmed that dendrimer biocides with 16 quaternary ammonium groups on their surfaces are over two orders of magnitude more potent than monofunctional counterparts against gram-negative bacteria, such as *Escherichia coli*. These biocides are also very effective against Gram-positive bacteria such as *Staphylocoecus aureus*, which are usually more susceptible to antimicrobials due to their less complex structures.

SUMMARY

Embodiments of the present invention include compositions and methods for sorbing and/or destroying dangerous substances such as chemical warfare agents, biological warfare agents, toxic industrial chemicals (TICs), or toxic industrial materials (TIMs). Some embodiments of the present invention include high surface area compositions and methods for using them to trap and/or destroy dangerous substances such as chemical warfare agents, biological warfare agents, toxic industrial chemicals (TICs), or toxic industrial materials (TIMs). Some embodiments of the invention include dendritic polymers, for example quaternary ammonium functionalized dendrimers and hyperbranched polymers.

According to one embodiment, the invention includes a quaternary ammonium functionalized dendritic polymer of formula I:

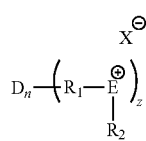

(Formula I)

wherein:
D is a dendrimer or a hyperbranched polymer;
n is the generation number of the dendrimer or the number of branches of the hyperbranched polymer;
z is an integer;
X is an anion;
$R_1$ is a linking group;
$R_2$ is hydrogen, an alkyl group having 1-32 carbon atoms, an aryl group having 1 to 32 carbon atoms or chloromethyl; and
E is any nitrogen containing heterocyclic or heteroaromatic ring system of which one nitrogen is covalently bonded to $R_1$ and $R_2$ and has a positive charge.

According to another embodiment, the invention includes a quaternary ammonium functionalized dendritic polymer of formula II:

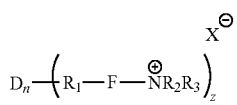

(Formula II)

wherein:
D is a dendrimer or a hyperbranched polymer;
n is the generation number of the dendrimer or the number of branches of the hyperbranched polymer;
z is an integer;
X is an anion;
$R_1$ is a linking group;
F—N is any nitrogen containing heterocyclic or heteroaromatic ring system in which at least one nitrogen in the ring is quaternized and bonded to $R_2$ and $R_3$ but not to $R_1$;
$R_2$ is hydrogen, an alkyl group having 1-32 carbon atoms, an aryl group having 1 to 32 carbon atoms or chloromethyl; and
$R_3$ is hydrogen, an alkyl group having 1-32 carbon atoms, an aryl group having 1-32 carbon atoms, or chloromethyl.

According to one embodiment, F—N is a piperazine cycle where $R_2$ is a methyl group and $R_3$ is a dodecyl group.

According to yet another embodiment, the invention includes a quaternary ammonium functionalized dendritic polymer of formula III:

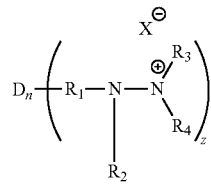

(Formula III)

wherein:
D is a dendrimer or a hyperbranched polymer;
n is the generation number of the dendrimer or the number of branches of the hyperbranched polymer;
z is an integer;
X is an anion;
$R_1$ is a linking group;
$R_2$ is hydrogen, an alkyl group having 1-32 carbon atoms, an aryl group having 1 to 32 carbon atoms or chloromethyl;
$R_3$ is hydrogen, an alkyl group having 1-32 carbon atoms, an aryl group having 1-32 carbon atoms, or chloromethyl; and
$R_4$ is hydrogen, an alkyl group having 1-32 carbon atoms, an aryl group having 1 to 32 carbon atoms or chloromethyl.

Formulas I, II, and III of the invention include a group $D_1$, defined as a dendrimer or a hyperbranched polymer. According to some embodiments, D may be, for example, a polyamidoamine dendrimer, a polyethylene oxide based dendrimer, a polypropylene imine based dendrimer, a silicon based dendrimer, a polyglycerol based hyperbranched polymer, a poly(ester amide) based hyperbranched polymer a silicon based hyperbranched polymer, or a hyperbranched polyol.

Formulas I, II and III of the invention include a group n, defined as the generation number of the dendrimer or the number of branches of the hyperbranched polymer. According to one embodiment of the invention, D is a dendrimer and n is an integer of 1 to 10. According to another embodiment, D is a hyperbranched polymer and the number of branches is 2 to 40. Formulas I, II, and III also include a group X, defined as an anion. According to some embodiments, X is fluoride, chloride, iodide, bromide, sulfate, sulfite, nitrate, chlorite, chlorate, hydroxide, carbonate, formate, perchlorate, hexafluorophosphate, or permanganate. Formulas I, II, and III also include a group $R_1$, defined as a linking group. $R_1$ may be any linking group that links the quaternary ammonium group to the dendrimer, including but not limited to —CO—, —CO—NH—, —CO—NH—$(CH_2)_a$— where a is an integer of 1 to 20, or —CO—NH-phenyl-$CH_2$, —$(CH_2)_b$— where b is an integer of 1 to 20. A quaternary ammonium functionalized dendritic polymer of the invention has about 1 to 100% functionality. The groups $R_2$, $R_3$, and $R_4$ of the formulas described herein may be hydrogen, an alkyl group having 1-32 carbon atoms, an aryl group having 1 to 32 carbon atoms or chloromethyl. In formula II, groups $R_2$ and $R_3$ are individually selected from hydrogen, an alkyl group having 1-32 carbon atoms, an aryl group having 1 to 32 carbon atoms or chloromethyl. In formula III, groups $R_2$, $R_3$, and R are individually selected from hydrogen, an alkyl group having 1-32 carbon atoms, an aryl group having 1 to 32 carbon atoms or chloromethyl.

Other embodiments of the invention include N-Halamine compounds including N-Halamine functionalized dendrimers and hyperbranched polymers. Other embodiments can include any combination of quaternary ammonium functionalized dendrimers and hyperbranched polymers with N-Halamine compounds including functionalized dendrimers and hyperbranched polymers. Other embodiments can include dendrimers and hyperbranched polymers functionalized with quaternary ammonium compounds and N-Halamines. Such dendritic polymers are useful for the capture and neutralization of biological warfare agents, chemical warfare agents, or other toxic materials.

It has been found that quaternary ammonium functionalized dendritic polymers and N-Halamine compounds including functionalized dendritic polymers are effective in the capture and neutralization of, for example, chemical agents, biological agents, and biologically generated toxins. Dendritic polymers can be dendrimers or hyperbranched polymers. One embodiment of the invention is a method of deactivating a toxic target agent comprising providing a composition comprising a quaternary ammonium functionalized dendritic polymer and an N-Halamine functionalized dendritic polymer onto a substrate, and placing the substrate in contact with a target agent selected from a chemical agent, a biological agent, a biologically generated toxin, a TIC and a TIM agent. Another embodiment of the invention is a method of treating an area contaminated with a toxic target agent comprising providing a composition comprising quaternary ammonium functionalized dendritic polymers and N-Halamine functionalized dendritic polymers or N-Halamine compounds to the contaminated area, wherein the toxic agent is a chemical agent, a biological agent, a biologically generated toxin, a TIC or a TIM agent. The invention also includes a method of capturing a target agent comprising providing a composition comprising a quaternary ammonium functionalized dendritic polymer of formula I, formula II or formula III onto a substrate and contacting the coated substrate with a target agent selected from a chemical agent, a biological agent, a biologically generated toxin, a TIC, and a TIM. Optionally an N-Halamine compound, N-Halamine functionalized dendritic polymer or N-Halamine functionalized dendritic polymer, together with a quaternary ammonium functionalized dendritic polymer are dispersed onto a substrate or surface, and the substrate contacts the target agent. In various embodiments, the dendritic polymers may be effective in both an aqueous media and against airborne toxic agents, e.g., the target may be in an aqueous media or may be airborne.

Another embodiment of the invention is a composition for the trapping and deactivating a toxic target agent comprising a quaternary ammonium functionalized dendritic polymer and an N-Halamine compound such as an N-Halamine functionalized dendritic polymer. Compositions of the present invention may be used to contact a toxic target agent selected from a chemical warfare agent, a biological warfare agent, a biologically generated toxin, a TIC and a TIM. The compositions may be effective, for example, in both an aqueous media and against airborne toxic agents.

Another embodiment of the present invention is a composition capable of reducing the effectiveness of a target toxic agent, the composition comprising a quaternary ammonium functionalized dendritic polymer and an N-Halamine functionalized dendritic polymer, the composition comprising an N-Halamine functionalized dendritic polymer, or the composition comprising an N-Halamine dispersed on high surface area substrates, or the composition comprising an N-Halamine in a powder or vapor form. According to some embodiments, an N-Halamine compound of the invention comprises a halogenated amine including but not limited to an oxidizolidinone, an imidizolidinone, or a hydantoin.

The invention further includes a coating composition comprising a quaternary ammonium functionalized dendritic polymer of formula I, formula II or formula III. The coating composition may further comprise an N-Halamine compound. According to some embodiments, the N-Halamine compound is an oxidizolidinone, an imidizolidinone, or a hydantoin. According to one embodiment, the coating composition of the invention further comprises an N-Halamine functionalized dendritic polymer comprising a plurality of halogenated amines selected from oxidizolidinones, imidizolidinones, hydantoins, and combinations thereof. The invention also includes a coated substrate comprising a substrate coated with such a coating composition. According to some embodiments, the substrate may be a coated polymeric bead, a metal or metal oxide particle, glass, a textile material, or a filter (e.g., an air filter).

Another embodiment of the present invention is a substrate material coated with a composition comprising a quaternary ammonium functionalized dendritic polymer of formulat I, II, or III. The substrate may be further coated with an N-Halamine compound such as an N-Halamine functionalized dendritic polymer, or an N-Halamine functionalized dendritic polymer. In the coating embodiments of the present invention, the substrate material may be a polymeric microsphere, a metal or metal oxide particle, a glass bead, a textile material, or another suitable material. Another embodiment of the present invention is a filter coated with a composition comprising a quaternary ammonium functionalized dendritic polymer and an N-Halamine compound or a quaternary ammonium functionalized dendritic polymer and an N-Halamine functionalized dendritic polymer, a filter coated with an N-Halamine dendritic polymer, or a filter (e.g., an air filter) coated with an N-Halamine composition such as small powder particles or vapor coating of N-Halamine. Another embodiment of the present invention is a textile material coated with a composition comprising a quaternary ammonium functionalized dendritic polymer and an N-Halamine compound or a quaternary ammonium functionalized dendritic polymer and an N-Halamine functionalized dendritic polymer, or a textile material coated with an N-Halamine functionalized dendritic polymer, or a textile material coated with an N-Halamine composition such as small powder particles or vapor coating of N-Halamine. In the composition embodiments and methods of the present invention both hyperbranched polymers and dendrimers may be functionalized.

Advantageously, the dendritic polymers in embodiments of the present invention as well as high surface area powders and vaporized forms of deactivating agents like N-Halamines and quaternary amines may be utilized as agents to trap and deactivate biological warfare agents, chemical warfare agents, toxic industrial chemicals (TICs), or toxic industrial materials (TIMs). Such high surface area trapping agents in powder, vapor, or linked to dendritic polymers may be provided to contact a toxic agent to be neutralized. Advantageously, these trapping agents may be applied or linked to an appropriate surface or substrate, such as a filter, fabrics, particles, beads, and walls. Such high surface area materials including dendritic polymers may be used to capture and neutralize (deactivate) biological (such as bacteria, viruses and spores), chemical warfare agents, and other toxic materials.

BRIEF DESCRIPTION OF THE DRAWINGS

Various aspects and applications of the present invention will become apparent to the skilled artisan upon consideration of the brief description of the figures and the detailed description of the invention, which follows.

DETAILED DESCRIPTION

Figure 1:
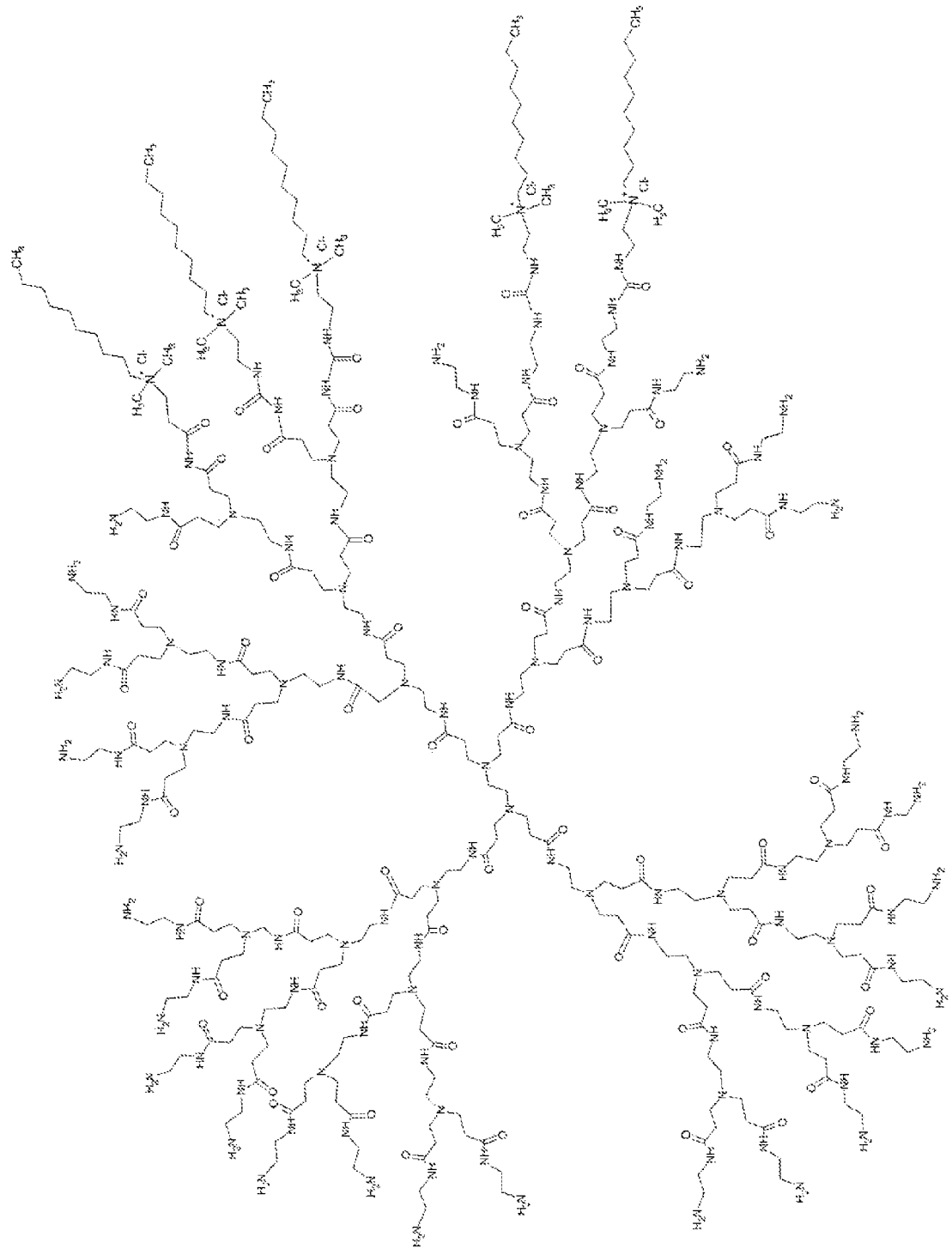
FIG. 1 illustrates a structure of a dendrimer includes one or more quaternary ammonium groups attached to the dendrimer.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "agent" is a reference to one or more agents and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred compositions, methods, devices, and materials are now described. All publications mentioned herein are incorporated by reference in their entirety. Nothing herein is to be construed as an admission that the invention is not entitled to antedate such disclosure by virtue of prior invention.

The terms "capturing", "trapping", "sorbing", as in "adsorption" and "chemisorption" and the like refer to the physical and/or chemical attachment, adhesion, or bonding of any such toxic agent to the dendritic polymers, vapor, powdered, or substrate containing N-Halamine and or quaternary ammonium compounds described in various embodiments of the present invention, Any such term may be used interchangeably herein.

The terms "deactivate", "deactivation", "decontaminate", "decontamination", "destroy", "destroying", "treat", "treating", "neutralize" and "neutralization" and the like are to be understood as meaning to render any such toxic agent inactive, ineffective, or substantially less effective for causing harm to life or health, and particularly human life or health. Thus such (deactivation) contact is of course to be for a sufficient time and under conditions which are sufficient to produce a reaction product having less toxicity than said toxic agent. Any such term may be used interchangeably herein.

Dendritic polymers are highly branched globular macromolecules which can be subdivided into the two different categories, namely dendrimers and hyperbranched polymers. Dendrimers can be highly uniform, three-dimensional, monodisperse polymers with a tree-like, globular structure. A dendrimer is a substantially or completely symmetrical, layered macromolecule that consists of three distinct areas: the polyfunctional central core or focal point, various radial layers of repeating units (so-called generations G), and the end groups, which are also termed peripheral or terminal groups. Hyperbranched polymers represent another class of globular, highly branched macromolecules which unlike dendrimers, exhibit polydispersity and irregularity in terms of branching and structure. Hyperbranched polymers can be prepared more cost effectively than dendrimers which can be advantageous.

Dendrimers are well defined, highly branched macromolecules that emanate from a central core. Example of suitable dendrimers include polyamidoamine ("PAMAM") dendrimers and polypropylene imine ("PPI") dendrimers. Dendriditic architecture brings a very high number of functional groups in a compact space. Examples of dendrimers include polyamidoamine dendrimers, such as quaternary ammonium functionalized dendrimers and N-Halamine (chloramine) functionalized dendrimers.

Dendrimers can be tailored to generate uniform or discrete functionalities and possess tunable inner cavities, surface moieties, sizes, molecular weights, and solvent interactions. Dendrimers may be synthesized by a convergent approach, see Tomalia, et al., Macromolecules, 20 at 1164 (1987). Alternatively, dendrimers may also be synthesized by a divergent approach, see Tang, et al., Bioconjugate Chem., 7 at 703-714 (1996), both herein incorporated by reference.

In the divergent approach, growth of dendrimers starts from a multi-functional core. Through a series of reaction and purification steps, dendrimers grow radially outwards. At different stages of the synthesis, dendrimers are identified by generations. As the generation increases, the number of functional groups, the size of the dendrimer, and the molecular weight of the dendrimer increase. Commercially available dendrimers, such as polyamidoamine (PAMAM) dendrimers from Dendritech Inc. (Midland, Mich., USA) are synthesized by the divergent approach.

In the convergent approach, dendrons, as parts of dendrimers, are synthesized according to the divergent approach and these dendrons are then coupled to a multifunctional core. An advantage of the convergent approach is that the chemistry of each dendron can be different, and distinct functional groups can be integrated into dendrimers at precise sites. The combination of discrete numbers of functionalities in one molecule and high local densities is advantageous for applications where a high surface contact area is important.

One example of a hyperbranched polymer that may be used to link one or more quaternary amines, N-halamines, or any combination of these is Hybrane® available from DSM Hybrane. Hybrane® is a hyperbranched poly(ester amide) based on a monomer made from reacting a cyclic anhydride with diisopropanolamine. Another polyester hyperbranched polymer is Boltorn, available from Perstorp.

The functionalized dendritic polymers of the present invention may be used to treat, destroy, deactivate, render ineffective, and/or neutralize toxic agents. The use of the dendritic polymers of the present invention may be used to decontaminate an area contaminated with a biological or chemical agent. The term "dendritic polymers" refers to both dendrimers, hyperbranched polymer, or any combination of dendrimer and hyperbranched polymers. Both subsets are suitable for the compositions and methods of the present invention and either may be used to the exclusion of the other in various embodiments of the invention.

Another embodiment of the present invention is a composition comprising quaternary ammonium functionalized dendritic polymers, N-Halamine (such as chloroamine, bromoamine, iodoamine) compounds including functionalized dendritic polymers, or any combination of these. Other embodiments of the present invention are coatings and coated substrates comprising quaternary ammonium functionalized dendritic polymers and/or N-Halamine functionalized dendritic polymers.

In the several method embodiments of the present invention, the use of dendritic polymers in the capture and neutralization of toxic agents may be accomplished by a solid-state system. A solid substrate in this system may be coated with the dendritic polymers of the present invention. Alternatively, the solid substrate may be coated with a combination of quaternary ammonium and or N-Halamine functionalized dendritic polymers, quaternary ammonium and or N-Halamine powders deposited on or into the substrate, quaternary ammonium and or N-Halamine vapors deposited on or into the substrate, or any combination of these. The use of dendritic polymers, powders, or vapors of these provides high surface functionality and a matrix that can be used to coat surfaces such as filters, liners, particles, fabrics, glass, metal, wood, plastic, and concrete. Examples of fabrics that may be coated include nylon, polyester, polyethylene, polypropylene, acrylic, acetate, olefin cotton, rayon, silk, wool blends thereof and any other natural or synthetic fabrics typically used as clothing or protective gear. Examples of particles that may be coated with the dendritic polymers, powders, and vapors, include polymeric microspheres, hollow glass beads, and any other suitable material, including nanoparticles. Additionally, the dendritic polymers may be used in traditionally sorbing equipment including a packed column.

Embodiments of the present invention include compositions and methods employing quaternary ammonium functionalized dendritic polymers (QAFDs). These dendritic polymers are PAMAM (poly(amidoamine)) based or can be polypropylene imine ("PPI") based dendritic polymers. N-Halamine functionalized dendritic polymers can also be PAMAM based. PAMAM dendrimers can be synthesized by the divergent method starting from ammonia or ehtylenediamine initiator core reagents. They can be constructed using a reiterative sequence consisting of (a) a double Michael addition of methyl acrylate to a primary amino group followed by (b) amidation of the resulting carbomethoxy intermediate with a large excess of ethylenediamine. In other embodiments one or more quaternary ammonium, N-Halamine, or any combination of these can be linked to a hyperbranched polymer via functional groups.

According to one embodiment, the invention comprises a quaternary ammonium functionalized dendritic polymer of formula I:

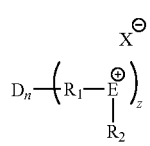

(Formula I)

wherein:
D is a dendrimer or hyperbranched polymer;
n is the generation number of the dendrimer or the number of branches of the hyperbranched polymer;
z is an integer;
X is an anion;
$R_1$ is a linking group;
$R_2$ is hydrogen, an alkyl group having 1-32 carbon atoms, an aryl group having 1 to 32 carbon atoms or chloromethyl; and
E is any nitrogen containing heterocyclic or heteroaromatic ring system of which one nitrogen is covalently bonded to $R_1$ and $R_2$ and has a positive charge.

According to another embodiment, the invention comprises a quaternary ammonium functionalized dendritic polymer of formula II:

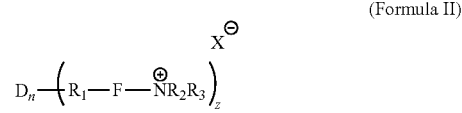

(Formula II)

wherein:
D is a dendrimer or hyperbranched polymer;
n is the generation number of the dendrimer or the number of branches of the hyperbranched polymer;
z is an integer;
X is an anion;
$R_1$ is a linking group;
F—N is any nitrogen containing heterocyclic or heteroaromatic ring system in which at least one nitrogen in the ring is quaternized and bonded to $R_2$ and $R_3$ but not to $R_1$;
$R_2$ is hydrogen, an alkyl group having 1-32 carbon atoms, an aryl group having 1 to 32 carbon atoms or chloromethyl; and
$R_3$ is hydrogen, an alkyl group having 1-32 carbon atoms, an aryl group having 1-32 carbon atoms, or chloromethyl.

The invention also includes, in one embodiment, a quaternary ammonium functionalized dendritic polymer of formula III:

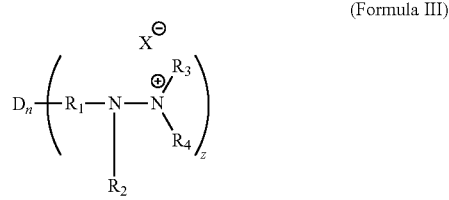

(Formula III)

wherein:
D is a dendrimer or hyperbranched polymer;
n is the generation number of the dendrimer or the number of branches of the hyperbranched polymer;
z is an integer;
X is an anion;
$R_1$ is a linking group;
$R_2$ is hydrogen, an alkyl group having 1-32 carbon atoms, an aryl group having 1 to 32 carbon atoms or chloromethyl;
$R_3$ is hydrogen, an alkyl group having 1-32 carbon atoms, an aryl group having 1-32 carbon atoms, or chloromethyl; and $R_4$ is hydrogen, an alkyl group having 1-32 carbon atoms, an aryl group having 1 to 32 carbon atoms or chloromethyl.

The compounds shown in formula I and II present new cyclic quaternary ammonium structures containing single or multiple nitrogen groups which can be converted into quaternary ammonium groups. The increase in the density of positively charged quaternary groups will enhance the capture of organisms which typically consist of negatively charged surfaces.

The quaternary ammonium structures of formula III are derived from hydrazines. Even though hydrazines are weaker bases than their corresponding amines by 1 to 3 powers of 10, they exhibit pronounced nucleophilic character (P. A. S. Smith, "Derivatives of Hydrazine and Other Hydronitrogens Having N—N Bonds", Benjamin/Cummings, Canada, 18-22 (1983)). The increased nucleophilicity exhibited by hydrazines has been attributed to the alpha effect. This effect is observed when two atoms with unshared electron pairs are bonded together (J. Aubort, R. Hudson and R. Woodcock, Tet. Lett., 2229 (1973) and T. Bruice A. Denzel, R. Huffman and A. Butler, J. Am. Chem. Soc., 89, 2106 (1967)). The repulsion between the two electron pairs raises the ground state energy thereby increasing the nucleophilicity. The unique electronic features of hydrazines make them particularly attractive for use in generating quaternary hydrazonium and N-halohydrazine species suitable for controlling the growth of microorganisms.

Formulas I, II and III include a linking group $R_1$. The linking group links the quaternary ammonium group to the dendritic polymer. The linking group is well known to those of skill in the art, and may include but is not limited to —CO—, —CO—NH—, —CO—NH—$(CH_2)_a$— where a is an integer of 1 to 20, or —CO—NH-phenyl-$CH_2$, —$(CH_2)_b$— where b is m integer of 1 to 20.

A quaternary ammonium functionalized dendritic polymer of the invention has about 1 to 100% functionality. The functionality is based on conversion of the end-groups (such as amine groups) of the base dendritic polymer to quaternary ammonium groups. The number of end-groups of the dendritic polymer ($D_n$) is determined by n, where n is an integer of 1 to 10 for dendrimers, and 2 to 40 for hyperbranched polymers. For example, for the generation 3 PAMAM dendrimers, n=3 and the number of amine end groups is 32. If 50% of the amine groups are converted to quaternary ammonium groups, then the quaternary ammonium dendritic polymer has a functionality of 50%.

One embodiment of the invention is a method for deactivating a toxic target agent that can include the acts of contacting a composition comprising a dendritic polymer functionalized with one or more quaternary ammonium compounds. In other embodiments the method includes the act of deactivating a toxic target agent that can include the acts of contacting a composition comprising a dendritic polymer functionalized with one or more N-Halamine compounds. In another embodiment, the method includes the acts of deactivating a toxic target agent that can include the acts of contacting a composition comprising a dendritic polymer functionalized with a combination of one or more quaternary ammonium compounds and N-Halamine compounds. The toxic target agent may be one or more of chemical agents, biological agents, biologically generated toxins, TICs or TIMs.

One embodiment of the invention is a composition that can include aerosolized beads coated with halogenated hydantoins for deactivating biological agent. In some embodiments the size of the bead can range from about 0.1 to about 100 microns; in other embodiments where a higher contact surface area is beneficial, the beads can have a size that ranges from about 0.1 to about 30 microns or from about 0.1 to about 20 microns. In some embodiments, the hydantoin can be 1,3-dichloro-5,5-dimethylhydantoin (DCDMH)

The aerosolized beads can be made from a variety of chemically and physically compatible materials. Examples of such materials can include but are not limited to polymers like poly(styrene-co-divinylbenzene), polymethylmethacrylate, and copolymers of polystyrene and polymethylmethacrylate, borosilicate glass or combinations of these. The beads can be either hollow or solid and the beads can have a density ranging from about 0.1 to about 2.6 $g/cm^3$.

In some embodiments the N-halamine can be made into a powdered form from an aerosol or milled powder and the aerosolized pure powder of N halamine used to neutralize aerosolized biological agents. Preferably the N-halamine is DCDMH powder having a particle size in the range of about 0.1 to about 35 microns, even more preferably from about 0.1 to about 20 microns. In some embodiments the hydantoin is vaporized and the gas or vapor form of halogenated hydantoins is used to neutralize aerosolized biological agents. Preferably the hydantoin is 1,3-dichloro-5,5-dimethylhydantoin (DCDMH).

The quaternary ammonium functional groups on the dendritic polymers can be used to provide a high concentration of positive charges that serve to "capture" the negatively charged toxic agents, such as bacterial spores. Without wishing to be bound by theory, the interactions between the functional groups and the agents are electrostatic interactions between the oppositely charged surfaces. Adhesion may also be enhanced by hydrophobic interactions between the hydrophobic-QAFD surface with the hydrophobic surface of the toxic agents, such as bacteria or spores. The QAFDs function as a capturing (adhesion) agent for the toxic agents upon contact. In another embodiment, the QAFDs function to provide antimicrobial protection against typical airborne bacteria. The QAFDs suitable for the present invention may have a molecular weight of about 1000 to about 100,000 and may be very monodisperse (typical polydispersity may be in the range of about 1.0002 to about 1.01).

In the case of dendrimers, the molecular weight can be determined by the generation (G) of the dendrimer selected. The surface functionality and molecular weight increase with the generation. Without wishing to be bound by theory, dendrimers with generation G0-G10 (e.g., PAMAM MW 517-934,720) may be functionalized with one or more quaternary ammonium, one or more N-Halamine groups, or any combination of these. For example, amine terminated G3 PAMAM dendrimers with molecular weight of 6909 has 32 surface functional groups. With complete functionalization of G3 PAMAM dendrimer with dimethyl decyl quaternary ammonium groups, the molecular weight is 15530. Functionalization of G4 and G5 dendrimers with 64 and 128 functional groups may also be suitable.

The quaternary ammonium functionalized dendritic polymers may be any number of compositions and molecular weights. Quaternary ammonium functionalized dendritic polymers may be synthesized according to any suitable method. For example, the methods described in C. Z. Chen, N. C. Beck Tan, P. Dhurjati, T. K. van Dyk, R. A. LaRossa, S. T. Cooper, "Quaternary Ammonium Functionalized Poly (propylene imine) Dendrimers as Effective Antimicrobials: Structure-Activity Studies," Biomacromolecules 2000 Fall; 1(3):473-80, herein incorporated by reference in its entirety, may be used to make the QAFDs of the present invention. Similar methods may be used to synthesize N-Halamine functionalized dendritic polymer as well as dendritic polymer comprising combinations of these deactivating agents.

Suitable QAFDs for embodiments of the invention may include for example dendrimers functionalized with up to 64 quaternary ammonium groups per molecule. Specific QAFDs may include dimethyldodecyl ammonium chloride functionalized poly(propyleneimine) ("PPI") generation 3 dendrimers. Methods described herein may be used to synthesize up to generation 5 dendrimers. Although a method is described using dimethyl dodecylamine, any number of dimethyl alkylamines ($C_8$, $C_{10}$, $C_{14}$ and $C_{16}$, for example) may be used.

The functionalization of dendritic polymers may consist of two steps. First, halogen (chlorine, bromine or iodine) functionality is introduced by reacting the primary amine groups of the polymer with a bifunctional chemical, such as 2-chloroethyl isocyanate, 2-bromoethyl isocyanate, or 2-iodoethylisocyanate. The halogen can then react with tertiary amines to form quaternary ammonium compounds.

A typical preparation procedure for a generation 3 dimethyl dodecylammonium functionalized PPI dendrimer may be described as follows. To a solution of 5.0 grams of PPI generation 3 dendrimer stripped with 500 mL of anhydrous toluene in 150 mL of anhydrous N,N-dimethylacetamide, 5.21 grams of 2-chlorethyl isocyanate may be added dropwise at room temperature. The mixture may be stirred overnight. After mixing 50.5 g of dimethyl dodecylamine, 150 mL of N,N-dimethylacetamide, and 150 mL of toluene may be added. The solution may be slowly heated to 80° C. for 72 hours. After heating, the solution may be concentrated to ca. 100 mL. The concentrated solution may be precipitated in acetone. The mixture may be filtered and dried in vacuum at 60° C., and the product may be obtained as a yellow solid material at about 70% yield.

The N-halamine functionalized dendritic polymers can act as a neutralizing agent in the present methods and compositions. The N-halamine functionalized dendritic polymers provide a high surface functionality of N-halamine groups, which provide a temporary storage of the halogen (chlorine, bromine, or iodine) in the solid dendritic polymer matrix until its release upon contact with the biological agent. N-halamines are effective biocidal agents and are capable of regeneration after use by treatment with halogen solution.

N-halamine functionalized dendritic polymers may be functionalized in any suitable manner. The N-halamines dendritic polymers may be any number of halogenated amines including oxidizolidinones, imidizolidinones and hydantoins. The dendrimers or hyperbranched polymers may include a plurality of functional groups, The N-halamines may be chlorinated, brominated, iodinated or some combination thereof. For example, a series of U.S. Patents by Worley, et al describe suitable compounds and methods. U.S. Pat. Nos. 5,490,983; 5,902,818; and 6,469,177 are herein incorporated by reference in their entirety. N-halamine functionalized dendritic polymers may be described as biocidal polymers comprising at least one cyclic N-halamine unit linked at a carbon atom wherein each N-halamine unit comprises a 4 to 7 membered ring, wherein at least 3 members of the ring are carbon, 1-3 members of the ring are a nitrogen heteroatom, and 0-1 member of the ring is an oxygen heteroatom. In the case of dendrimers, the periphery of dendrimers with generation G0-G10 may be functionalized with a variety of N-Halamine compounds by reaction of the functional groups of each compound with the appropriate moieties, such as reaction of an amine-terminated dendrimer with carboxylic acid, or thionyl chloride. Amine terminated G3 PAMAM dendrimers may be functionalized via reaction with 5-hydantoin acetyl chloride. The hydantoin-terminated dendrimers can then be chlorinated post-reaction by dipping coated substrates in aqueous solution of chlorine bleach (5.25% NaOCl). Alternatively, chlorination of the hydantion can be achieved by treating with chlorine gas in a basic solution such as sodium hydroxide. Functionalized hyperbranched polymers may be treated in a similar manner.

Hyperbranched polymers may be prepared in one-step procedures, most commonly by polycondensation of $AB_x$ monomers, as reported by Seiler, Matthias, "Dendritic Polymers—Interdisciplinary Research and Emerging Applications from Unique Structural Properties," Chem. Eng. Technol., 25 (2002) 3, herein incorporated by reference in its entirety. Apart from polycondensation, addition polymerization of monomers that contain an initiating function and a propagating function in the same molecule as well as ring opening polymerization of cyclic latent $AB_2$-type monomers can be applied for the synthesis of hyperbranched macromolecules. Functionalization of hyperbranched polymers is generally the same as for dendrimers, as is know by one skilled in the art.

The present systems use the dendritic polymers for both the capture and neutralization of biological and/or chemical agents. The use of the two types of functionalized dendritic polymers provides moieties for both purposes. The moieties which act to attach the toxic agent and then neutralize the agent are chemically bound to the surface of the dendritic polymers.

Coating solutions of about 1-50 wt % of the QAFD and an N-halamine dendritic polymer or the QAFD and an N-Halamine compound such as DCDMH may be used to coat air filter substrates. The loading onto a substrate may be from about 0.5 to about 100 wt %. The capture and neutralization of biological agents (specifically *Bacillus globigii*, also known as *Bacillus atrophaeus*) may be accomplished using substrates coated separately with each functionalized dendritic polymer. Mixtures of the two dendritic polymers may also be coated or coated as bi-layers or multiple molecular layers using the layer by layer system.

The QAFD dendritic polymers increase the capture of spores on the filter, but are not necessarily sporicidal. The N-halamine dendritic polymers are sporicidal. Coated filters containing a mixture of the QAFD and the N-halamine compound 1,3-dichloro-5,5-dimethylhydantoin (1:1 weight ratio) showed that the efficacy of the capture and subsequent neutralization of the spores on the filter was increased. Mixtures of the coatings maybe applied as a single layer, or first coated with the N-halamine functionalized dendritic polymer, then with the QAF-dendritic polymer on the surface.

In the method embodiments of the present invention, a composition that includes one or more quaternary ammonium compounds, one or more N-Halamines, or any combination of these as dendrimers, powders, or vapors can be provided to a suitable substrate. The coated substrate is next placed in contact with the target agent selected from the group consisting of chemical agents, biological agents, and biologically generated toxins. A method for deactivating a liquid or vapor phase target agent comprises contacting the N-halamine functionalized dendritic polymers, powders, or vapors and or QAFDs with the toxic target agent such that the target agent contacts the N-Halamine or quaternary ammonium compound and is deactivated by them. Vapor phase target agent(s) may, for example, be solubilized in an appropriate solvent through any (known) means and the resultant solution may be passed over N-halamine dendritic polymers and QAFDs. The present invention in an additional aspect provides a method for reducing or eliminating unwanted or undesired stockpiles of a toxic chemical agent susceptible to deactivation (e.g oxidation), which comprises deactivating a toxic chemical agent by contacting the toxic chemical agent (e.g. in a confining means) with the functionalized dendritic polymers (i.e. with a deactivating amount of a halogenated resin). Such contact is of course to be for a sufficient time and under conditions which are sufficient to produce a reaction product having less toxicity than said toxic chemical agents The confining means may be a sealed container, a chromatographic like column packed with halogenated resin, or any other suitable chamber, trap, or vessel.

The dendritic polymers may be attached to various substrates by covalent bonds or by electrostatic interactions between charged surfaces. The dendritic polymers may be attached to various substrates using a layer-by-layer technique. For example, a substrate may first be coated with a layer comprising the N-halamine functionalized dendritic polymers. The substrate may then be coated with an outer layer comprising QAFDs. In several embodiments, the dendrimers may be combined with hyperbranched polymers. The N-halamine dendritic polymers and/or the QAFDs may be optionally decorated with metals and metal oxides for improved performance. Metals include silver, copper and zinc. Metal oxides include $TiO_2$, $Al_2O_3$, MgO, and CaO. The use of metals and metal oxides in the destroying biological agents have been described by Koper et al in U.S. Pat. No. 6,653,519, herein incorporated by reference. Additionally, dendritic polymers of the present invention may also by functionalized to include iodinated moieties described in U.S. Pat. No. 6,727,400, herein incorporated by reference.

The dendritic polymers may be effective against chemical agents, biological agents, and biologically generated toxins, such as bacteria, spores, fungi, viruses, and toxins. Examples of bacterium include gram positive bacterium such as *B. globigii, B. cereus,* and *B. subtilis*. The dendritic polymers may also be effective against gram negative bacterium such as *E. coli* and *E. herbicola*.

Some potent biological agents include the following: bacteria such as *Bacillus anthracis* (anthrax) and *Yersinia pestis* (plague); viruses such as variola virus (small pox) and flaviviruses (hemorrhagic fevers). Some potent chemical agents include: blister or vesicant agents such as mustard agents; nerve agents such as ethylphosphonothiolate (VX); lung damaging or hoking agents such as phosgene (CG); cyanogen agents such as hydrogen cyanide; incapacitants such as 3-quinuclidinyl benzilate; riot control agents such as CS (malonitrile); smokes such as zinc chloride smokes, and some herbicides such as 2,4-D (2,4-dichlorophenoxy acetic acid). The chemical warfare agents include among other substances a variety of organophosphorus and organosulfur compounds. One commonly known chemical warfare agent is Bis-(2-chloroethyl) sulfide, also known as HD. The chemical warfare agents commonly known as G-agents are examples of highly toxic nerve agents; they include TABUN (GA), SARIN (GB), and SOMAN (GD); GD is pinacolyl methylphosphonofluoridate. The C-agents are broadly organic esters of substituted phosphoric acid.

The dendritic polymers, powders, and vapors that can include the quaternary ammonium compounds and or N-Halamines may be effective against a virus, such as a MS2 virus, or a fungus. The dendritic polymers may be effective against toxins selected from the group consisting of Aflatoxins, Botulinum toxins, *Clostridium perfringens* toxins, Conotoxins, Ricins, Saxitoxins, Shiga toxins, *Staphylococcus aureus* toxins, Tetrodotoxins, Verotoxins, Microcystins (Cyanginosin), Abrins, *Cholera* toxins, Tetanus toxins, Trichothecene mycotoxins, Modeccins, Volkensins, Viscum album Lectin 1, Streptococcal toxins, Pseudomonas A toxins, Diphtheria toxins, *Listeria monocytogenes* toxins, *Bacillus anthracis* toxic complexes, *Francisella tularensis* toxins, whooping cough pertussis toxins, *Yersinia pestis* toxic complexes, *Yersinia enterocolytica* enterotoxins, and *Pasteurella* toxins.

The dendritic polymers, powders, and vapors that can include the quaternary ammonium compounds and or N-Halamines may be effective against TICs and TIMs. These can be harmful to humans exposed in an accidental or intentional (terrorism) release. TICs and TIMs can take the form of solids, liquids, gases, vapors, dusts, fumes, fibers and mists, Some of the most dangerous TIC threats include: ammonia; arsine; boron trichloride; boron trifluoride; carbon disulfide; chlorine; 2-chlorovinylarsonous acid; diborane; diethyl methylphosphonate; diisopropylaminoethyl mercaptan; diisopropylaminoethyl methylphosphonthioic acid; ethyl methylphosphonic acid; ethylene oxide; fluorine; formaldehyde; hydrogen bromide; hydrogen chloride; hydrogen cyanide; hydrogen fluoride; hydrogen sulfide; lewisite oxide; Methyphosphinic acid; nitric acid, fuming; Phosgene; phosphorus trichloride; pinacolyl methylphosphonate; sulfur dioxide; sulfuric acid; thiodiglycol; or tungsten hexafluoride.

Practice of the invention, including additional preferred aspects and embodiments thereof, will be more fully understood from the following examples and discussion, which are presented for illustration only and should not be construed as limiting the invention in any way.

EXAMPLE 1

Preparation of G3 PAMAM quaternary ammonium functionalized dendrimer as illustrated in FIG. 1. G3 PAMAM dendrimers with quaternary ammonium groups consisting of dimethyl ($CH_3$) and decyl ($C_{10}H_{20}$) groups were synthesized via a two-step process. In a 250 ml round-bottom flask equipped with a magnetic stir bar, the PAMAM dendrimer (ethylene diamine core with 32-$NH_2$) was lyophilized in methanol and kept under vacuum overnight. The obtained solid dendrimer was weighed (6.24 g, 0.903 mmol; 28.9 mmol of —$NH_2$ groups) and 1-methyl-2-pyrrolidinone [NMP] (100 mL) was added and stirred for 2 hours under nitrogen. The 2-chloroethyl isocyanate (3.25 g, 30.8 mmol) was added dropwise over 5 minutes to the dendrimer solution and stirred for an additional 20 hours under nitrogen. N,N-dimethyldecylamine (26.78 g, 144.5 mmol) was added dropwise over 60 minutes to the well-stirred solution and the heated to 80° C. and stirred for 73 hours. The mixture was dialyzed once in water, and then three times in a mixture of methanol and dichloromethane (Spectra/Por 7; MWCO 3500). Volatile solvents were removed by rotary evaporation and the obtained modified dendrimer was dried by lyophilization under vacuum. The yield was 28% (4.11 g, 0.253 mmol).

Characterization: $^1$H NMR in $CD_3OD$: 3.60 ppm (—NH—$CH_2$—$CH_2$—NH—CO—NH—$CH_2CH_2$—N—$C_{10}H_{21}$); 3.44 ppm (—CO—N—$CH_2$—$CH_2$—N—$CH_2$—$C_9H_{19}$); 3.25 ppm (—CO—NH—$CH_2CH_2$—N=); 3.17 ppm (N $CH_3$); 2.80 ppm (=N—$CH_2CH_2$—CONH—($CH_2$)$_2$—N=); 2.60 ppm (—CO—NH—$CH_2CH_2$—N=); 2.38 ppm (=N—$CH_2CH_2$—CONH—($CH_2$)$_2$—N=); 1.80 ppm (—N—$CH_2$ $CH_2C_8H_{17}$); 1.30-1.39 ppm (—N—$CH_2CH_2C_7H_{14}CH_3$); 0.89 ppm (—$C_9H_{18}$—$CH_3$). $^{13}$C NMR in $CD_3OD$: 175.0 and 174.5 ppm (=N—$CH_2CH_2$—CO—NH—); 160.5 ppm (—NH—CO—NH—); 65.9 ppm (—N—$CH_2$—$C_9H_{19}$); 64.0 ppm (—CO—N—$CH_2CH_2$—N—$C_{10}H_{21}$); 53.4 ppm (—CO—NH—$CH_2CH_2$—N=); 52.5 and 51.6 ppm (N$CH_3$); 51.1 ppm (=N—$CH_2CH_2$—CONH—($CH_2$)$_2$—N=); 40.7 ppm (—NH—CH$_2$CH$_2$—NH—CO—NH—CH$_2$CH$_2$—N—C$_{10}$H$_{21}$); 38.6 ppm ($\overline{\text{—CO—NH—CH}_2\text{CH}_2\text{—N}=}$); 35.2 ppm (—CO—NH—CH$_2$CH$_2$—N—$\overline{\text{C}_{10}\text{H}_{21}}$); 34.8 ppm (=N—CH$_2$CH$_2$—$\overline{\text{CONH}}$—(CH$_2$)$_2$—N=); 23.6-33.0 ppm (—N—CH$_2\overline{\text{C}_8\text{H}_{16}}$CH$_3$); 14.6 ppm (—C$_9$H$_{18}$—CH$_3$). The internal $\overline{\text{repeat unit}}$ of PAMAM dendrimer is $\overline{\text{symbolized}}$ by the following: (—CH$_2$CH$_2$—CO—NH—CH$_2$CH$_2$—N=).

EXAMPLE 2

Figure 2:
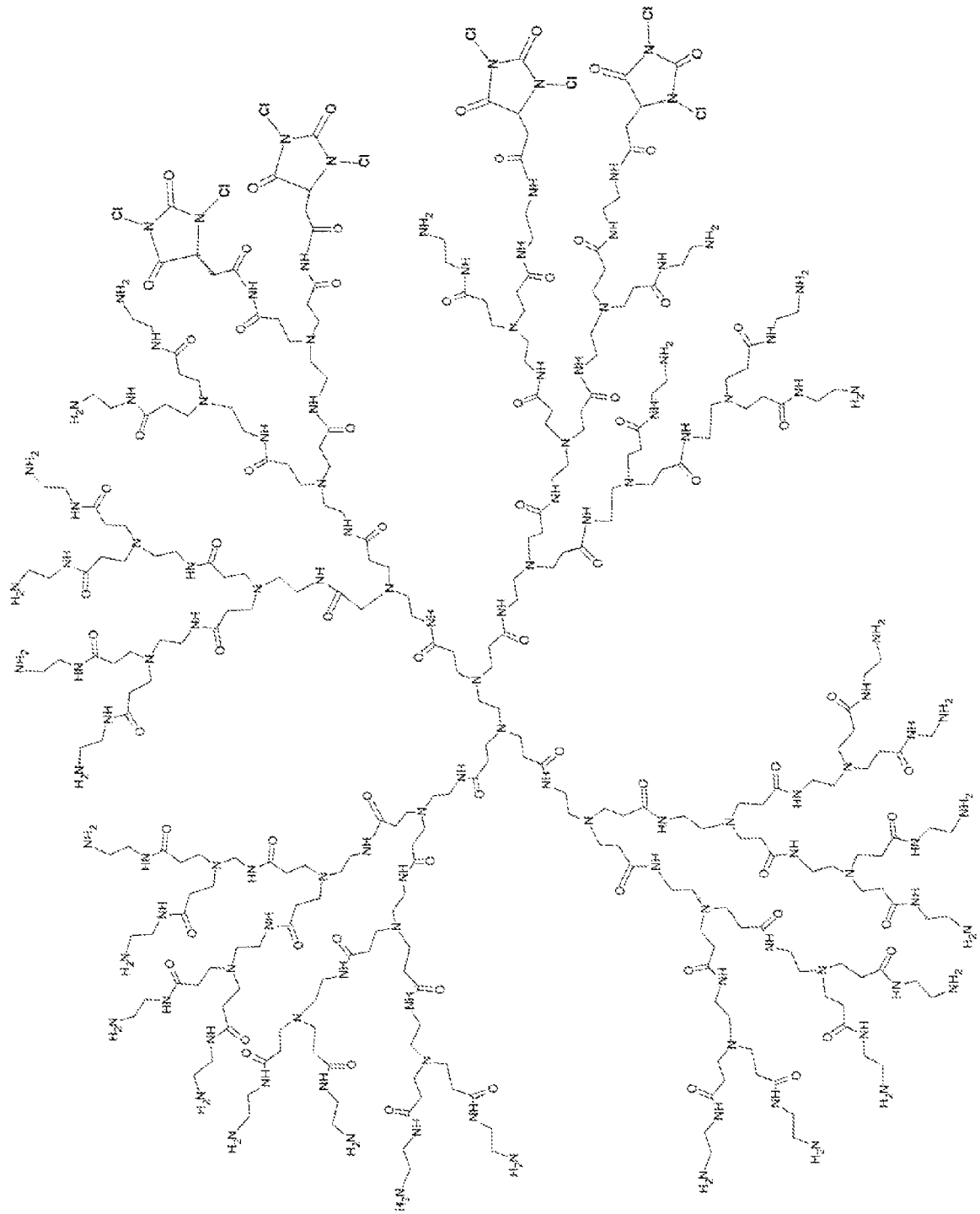
FIG. 2 illustrates a structure of a dendrimer that includes one or more N-Halamine functional groups attached to the dendrimer.

Preparation of G3-PAMAM N-Halamine functionalized dendrimer as illustrated in FIG. 2. G3-PAMAM dendrimer (ethylene diamine core with 32-NH$_2$) was functionalized by the reaction with 5-hydantoin acetyl chloride. The acetyl chloride was prepared by the reaction of 5-hydantoin acetic acid with thionyl chloride by refluxing for 5 days according to the following procedure. In a 500 ml round-bottom flask containing a magnetic stir bar and reflux condenser, thionyl chloride (250 ml, 408 g, 3.43 moles) was added to 5.52 g (34.9 mmol) 5-hydantoin acetic acid. The reaction mixture was heated to 89° C. in an oil bath and refluxed for 43 hours. The reflux condenser was removed and replaced with a short-path distillation apparatus to remove the thionyl chloride solvent by distillation at ambient pressure until distillate collection ceased. The remaining thionyl chloride was removed by vacuum pump. The residue in the reaction flask was dissolved in hot ethyl acetate. The unreacted starting material did not dissolve in the ethyl acetate. The hot ethyl acetate was gravity filtered into a 100 ml round-bottomed flask, and the solvent was removed by rotary evaporation. The acid chloride product was dried briefly under vacuum pump. 1.37 g (7.76 mmol, 22% yield) was obtained. $^1$H-NMR analysis of the product indicated about 67% conversion to the acid chloride.

In a 100 ml round-bottomed flask equipped with a magnetic stir bar, the G3 EDA core PAMAM dendrimer was lyophilized in methanol and kept under vacuum overnight. The obtained solid dendrimer was weighed (1.0052 g, 0.1454 mmol; 4.6528 mmol of —NH$_2$ groups) and anhydrous 1-methyl-2-pyrrolidinone [NMP] (20 ml) was added and mechanically agitated for 1 hour to dissolve the dendrimer. Triethylamine (1.30 ml, 0.944 g, 9.33 mmol) was added to the PAMAM in NMP solution by pipette. A 25 ml pressure-equalized addition funnel was placed on the flask, with a nitrogen inlet. The 5-hydantoin acetyl chloride was dissolved in a mixture of 13 ml anhydrous NMP and 1 ml DMSO and added to the addition funnel. The acid chloride solution was added dropwise over 90 minutes to the well-stirred solution. With each drop of acid chloride that was added to the reaction mixture increasing amounts of precipitate appeared. After two hours of labored stirring, 10 ml water was added to the reaction mixture, which caused the precipitate to dissolve. The reaction mixture was stirred for an additional 24 hours under a nitrogen flow. The reaction mixture was dialyzed three times in water (Spectra/Por 7; MWCO 3500). The water was removed by rotary evaporation and the product was dried by lyophilization under vacuum to yield 1.84 g of solid dendrimer.

EXAMPLE 3

Figure 3:
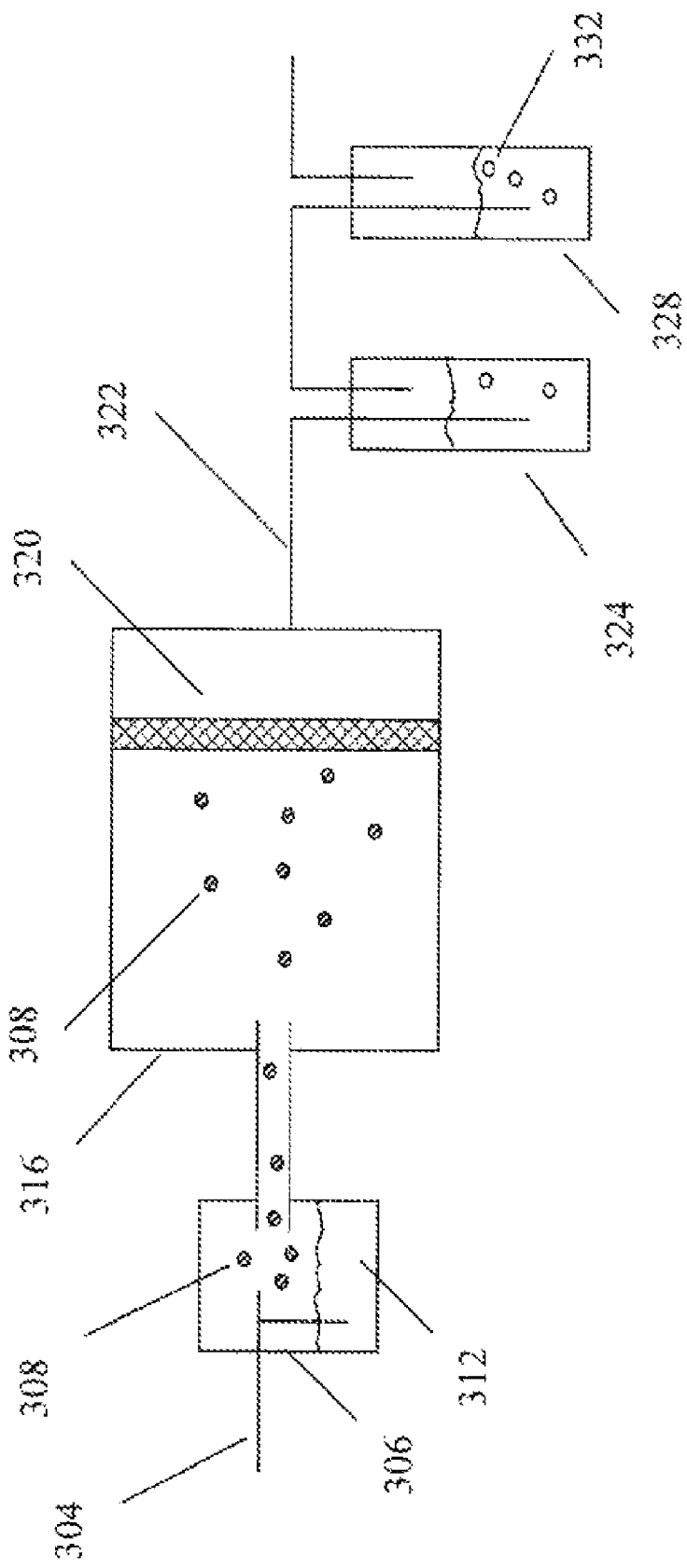
FIG. 3 is an illustration of a chamber that can be used for testing of porous substrates coated with compositions of the present invention; a carrier gas flows through a conduit 304 into a chamber 306 that can be used to form an aerosol of a toxic agent 308, such as a chemical or biological warfare agent, TIC, or TIM, that enters a test chamber 316 where a substrate 320 contacts the aerosolized toxic agent 308 and removes all or a portion of the agent from the carrier gas; impingers 324 and 328 are positioned downstream of the substrate 320 and can be used to trap and quantify the amount of agent removed from the carrier gas exhausted from the system 332.

Testing Set-Up as illustrated in FIG. 3. The aerosol chamber used for testing was assembled in-house and modeled after a bioaerosol chamber designed and published by the US Army RDEC Natick Soldier Center (Stote 2003). The set-up incorporates a Collison Nebulizer attached to a high-pressure cylindrical glass chamber. At the head of the chamber (right), a three-neck glass top is secured via a metal clamp. The sample is held between two plastic sheets that are clamped between the chamber and the glass top. A single outlet from the top 322 is attached to an impinger 324 containing buffer solution. The high pressure forces the aerosol 308 to flow through the air-filter 320 and bubble through the buffer solution contained in the impingers 324 and 328 where the spores that penetrate the filter (not shown) are subsequently trapped.

Testing using aerosolized BG spores. The treated filter substrates were placed in the sample holder and the chamber tightly sealed using a metal clamp. The sporicidal efficacy was tested using *Bacillus globigii* spores (BC), which were obtained from the U.S. Army's Dugway Proving Grounds Facilities. Stock suspensions of BG spores in phosphate buffer saline were prepared (10$^6$, 10$^5$ and 10$^4$ CFU/mL). The impingers were filled with 150 mL of 0.02 M sodium thiosulfate/phosphate buffer to sample the aerosol that passes through the filter. After 10 minutes, the filter sample was removed, placed in 25 mL of 0.02 M sodium thiosulfate/phosphate buffer solution, allowed to sit for 1-10 minutes and then vigorously shaken (using a vortex machine) for 5 minutes. Control samples were run with no filter and with uncoated filter substrates. For the neutralization experiments, excess free chlorine was quenched using the sodium thiosulfate added to the buffer prior to analysis.

Culture Based Data Analysis. Standard plating techniques were employed to analyze the samples obtained from the impingers and from the filter substrates. Four to five serial dilutions of the stock BG suspension were prepared and a volume of 0.1 mL plated onto nutrient agar. Two or three volumes (1.0 ml, 0.1 mL and 0.01 mL) of the buffer samples were plated onto nutrient agar plates. All samples were incubated at 37° C. for 24-48 hours and counting techniques were used to determine the spore concentrations reported in Colony Forming Units per mL (CFU/mL) and total spores (counts).

EXAMPLE 4

Testing of efficacy of capture of G3 PAMAM quaternary ammonium functionalized dendrimers coated onto MERV 8-rated air-filter substrates. Test substrates were spray coated with 5 wt % solutions in CH$_2$Cl$_2$/DMAC (1.6:1) of the quaternary ammonium PAMAM dendrimer (prepared in Example 1). The untreated filter was used as the control. Table 1 provides a summary of the data obtained from culture based analysis (spore counts as colony forming units (CFU)) of the tested filter substrate and samples collected from the two impingers connected in series.

TABLE 1

| Capture of BG spores using QUAT-PAMAM Dendrimer-Coated Filters | | |
|---|---|---|
| Sample | Spores captured on filter (%)[b] | Reduction in spore penetration (%)[c] |
| Untreated filter (control)[a] | 84.7 | — |
| QUAT-PAMAM filter | 95.6 | 52 |

[a]Average of 4 runs
[b](# spores on filter/total #captured) × 100]
[c] 00 − [(# spores on QUAT filter/# spores on control filter) × 100]

EXAMPLE 5

Testing of efficacy of neutralization of G3 PAMAM N-Halamine functionalized dendrimers coated onto vent air filter (Web Products) substrates. Data obtained for the filter samples treated with the N-Halamine functionalized PAMAM dendrimer (N-HAL PAMAM) is shown in Table 2.

TABLE 2

Neutralization of BG Spores using N-Halamine Dendrimer-Coated Filters

| Sample | Spores Neutralized on filter (%)[a] | Reduction in spore penetration (%)[b] |
|---|---|---|
| Uncoated filter (control) | 0 | — |
| N-HAL PAMAM dendrimer | 99.9 | 80 |

[a]100 − [(# spores on N-HAL filter/# spores on control) × 100]
[b]100 − [(# spores on QUAT filter/# spores on control filter) × 100]

The data in Table 2 shows 99.9% neutralization of spores on the coated N-Halamine dendrimer filter, and 80% reduction in the number of viable spores that penetrated the filter compared to the control (uncoated) filter.

EXAMPLE 6

Testing of capture and neutralization of a blend of G3 PAMAM quaternary ammonium functionalized dendrimer and 1,3-dichloro-5,5-dimethylhydantion (DCDMH). Test substrates used were MERV 8-rated air-filter substrates, which were spray coated with solutions of the quaternary ammonium PAMAM dendrimer and DCDMH in $CH_2Cl_2$/DMAC (1.6:1). The untreated filter was used as the control. Table 3 provides a summary of the data obtained from culture-based analysis (spore counts as colony forming units (CFU)) of the tested filter substrate and samples collected from the two impingers connected in series after aerosolization for 10 minutes.

TABLE 3

Capture and Neutralization of BG Spores using QUAT and N-Halamine-Coated Filters

| Sample | Spores captured on filter (%)[a] | Spores Neutralized on filter (%)[b] |
|---|---|---|
| Uncoated filter (control) | 84.7 | 0 |
| QUAT-PAMAM dendrimer | 95.6 | 0 |
| QUAT-PAMAM dendrimer:DCDMH (1:2) | 95.8 | 96.3 |

[a][#spores on filter/total #captured] × 100
[b][#spores on filter/# spores on control] × 100

The data illustrates that N-Halamine based compounds are effective sporicides for BG spores. The data shows after 10 minutes, 96% neutralization of viable BG spores captured on the filters coated with a mixture of QUAT-PAMAM dendrimer and DCDMH, compared to the control (uncoated) filters. In addition, the combination of the QAFD and N-Halamine effectively reduces the number of viable spores that penetrate the filter.

EXAMPLE 7

Testing of the neutralization efficacy of 1,3-dichloro-5,5-dimethylhydantoin coated on a nominal size of 8 μm poly(styrene-co-divinylbenzene) beads in air. First, MS-2 virus was aerosolized in a 1 $m^3$ chamber. Then, the dry aerosols of the poly(styrene-co-divinylbenzene) beads coated with 1,3-dichloro-5,5-dimethylhydantoin were introduced into the chamber. The live population of MS-2 virus in the chamber was reduced to 0.1 and 0.001% of the initial population after 5 min and 10 min, respectively (See Table 4).

TABLE 4

Plaque Forming Unit Count Data for the Neutralization of MS-2 in Air Using 1,3-dichloro-5,5-dimethylhydantoin Coated Poly(styrene-co-divinylbenzene) beads.

| Exposure Time (min) | MS-2 (PFU/$m^3$)[a] | Log Reduction[b] |
|---|---|---|
| 0 | $2.9 \times 10^{10}$ | — |
| 5 | $3.1 \times 10^7$ | 3.0 |
| 10 | $3.1 \times 10^5$ | 5.0 |

[a]plaque forming unit(PFU)
[b]log reduction = −log(PFU at time t/PFU at time 0)

EXAMPLE 8

Testing of the neutralization efficacy of 1,3-dichloro-5,5-dimethylhydantoin coated on a nominal size of 8 μm poly(styrene-co-divinylbenzene) beads in water. BC spores and poly(styrene-co-divinylbenzene) beads coated with 1,3-dichloro-5,5-dimethylhydantoin were mixed in phosphate buffered saline solution. The viable spore counts after a certain exposure time were shown in Table 5.

TABLE 5

Viable Spore Count Data for the Neutralization of BG Spores in Water Using 1,3-dichloro-5,5-dimethylhydantoin Coated Poly(styrene-co-divinylbenzene) Beads.

| Exposure Time (min) | Spore Concentration (CFU/mL)[a] | Log Reduction[b] |
|---|---|---|
| 0 | $1.0 \times 10^6$ | — |
| 1 | 200 | 3.7 |
| 2 | <1 | >6.0 |
| 5 | <1 | >6.0 |
| 10 | <1 | >6.0 |

[a]colony forming unit (CFU)
[b]log reduction = −log(CFU at time t/CFU at time 0)

EXAMPLE 9

Quaternization of the hyperbranched (DSM Hybrane) polymer with a hexahydrophthalic core and methyl piperazine endgroup using dodecyl iodine to yield quaternary ammonium hyperbranched polymer. We prepared a quaternary ammonium functionalized dendritic polymer with the following structure:

$$\text{HBP} \underset{}{\overset{O}{\diagdown}} \left( N \diagup \diagdown N^+ \diagdown_{C_{12}H_{25}}^{CH_3} I^- \right)_{16}$$

where HBP is a methyl piperazine terminated Hybrane® hyberbranched polymer.

EXAMPLE 10

Testing of the efficacy of neutralization of *Bacillus globigii*.
Table 6 summarizes data showing the neutralization of *Bacillus globigii* spores using the quaternary hyperbranched polymer shown in Example 9 in aqueous media.

TABLE 6

Neutralization of Bg Spores using Quaternary Ammonium Functionalized Hyperbranched Polymer (Example 9) in aqueous media

| Exposure Time (hr) | Bg Spores (CFU/mL)[a] | % Reduction[b] |
|---|---|---|
| 0 | $1.41 \times 10^6$ | — |
| 0.5 | $3.0 \times 10^5$ | 78.4 |
| 24 | $1.3 \times 10^5$ | 90.9 |

[a] colony forming units (CFU)
[b] % reduction = 100 − [(CFU at time t/CFU at time 0) × 100]

Table 7 summarizes data showing the neutralization of *Bacillus globigii* spores using the quaternary hyperbranched polymer shown in Example 9. In this case, the polymer was coated onto glass slides (2.5 cm×1 cm) from a 10 wt % methylene chloride solution. The slides were dried at room temperature overnight before testing.

TABLE 7

Neutralization of Bg Spores using Quaternary Ammonium Functionalized Hyperbranched Polymer coated onto glass slides

| Exposure Time (hr) | Bg Spores (CFU/mL)[a] | % Reduction[b] |
|---|---|---|
| 0 | $1.48 \times 10^5$ | — |
| 1 | $5.2 \times 10^4$ | 65.0 |

[a] colony forming units (CFU)
[b] % reduction = 100 − [(CFU at time t/CFU at time 0) × 100]

Table 8 summarizes data showing the neutralization of *Bacillus globigii* spores using a 1:1 mixture of the quaternary hyperbranched polymer shown in Example 9 and DCDMH. In this case, the mixture was coated onto glass slides (2.5 cm×1 cm) from a 20 wt % methylene chloride solution. The slides were dried at room temperature overnight before testing.

TABLE 8

Neutralization of Bg Spores using a mixture of Quaternary Ammonium Functionalized Hyperbranched Polymer and DCDMH coated onto glass slides

| Exposure Time (hr) | Bg Spores (CFU/mL)[a] | % Reduction[b] |
|---|---|---|
| 0 | $1.55 \times 10^5$ | — |
| 1 | 0 | >99.99 |

[a] colony forming units (CFU)
[b] % reduction = 100 − [(CFU at time t/CFU at time 0) × 100]

While preferred embodiments have been described in details variations may be made to these embodiments without departing from the spirit or scope of the attached claims.

What is claimed is:

1. A functionalized dendritic polymer for sorbing and destroying dangerous substances selected from the group consisting of chemical warfare agents, biological warfare agents, toxic industrial chemicals (TICs), and toxic industrial materials (TIMs), said functional dendritic polymer being of Formula II:

$$D_n\text{---}\!\left(R_1\text{---}F\overset{\oplus}{\text{---}}\!NR_2R_3\right)_z \quad X^{\ominus} \quad \text{(Formula II)}$$

wherein:
D is a dendrimer or hyperbranched polymer;
n is the generation number of the dendrimer or the number of branches of the hyperbranched polymer;
z is an integer that is not zero;
X is an anion;
$R_1$ is a linking group;
F—N is any nitrogen containing heterocyclic or heteroaromatic ring system in which at least one nitrogen in the ring is quaternized and bonded to $R_2$ and $R_3$ but not to $R_1$;
$R_2$ is a hydrogen, an alkyl group having 1-32 carbon atoms, an aryl group or chloromethyl; and
$R_3$ is a hydrogen, an alkyl group having 1-32 carbon atoms, an aryl group, or chloromethyl.

2. The functionalized dendritic polymer of claim 1, wherein D is a polyamidoamine dendrimer, a polyethylene oxide based dendrimer, a polypropylene imine based dendrimer, a silicon based dendrimer, a polyglycerol based hyperbranched polymer, a silicon based hyperbranched polymer, or a hyperbranched polyol.

3. The functionalized dendritic polymer of claim 1, wherein the number of branches n is an integer of 2 to 40 and wherein D is a hyperbranched polymer.

4. The functionalized dendritic polymer of claim 1, wherein X is fluoride, chloride, iodide, bromide, sulfate, sulfite, nitrate, chlorite, chlorate, hydroxide, carbonate, formate, perchlorate, hexafluorophosphate, or permanganate.

5. The functionalized dendritic polymer of claim 1, wherein $R_1$ is —CO—, —CO—NH—, —CO—NH—$(CH_2)_a$— where a is an integer of 1 to 20, or —CO—NH-phenyl-$CH_2$, —$(CH_2)_b$— where b is an integer of 1 to 20.

6. The functionalized dendritic polymer of claim 1, wherein $R_2$ and $R_3$ are independently alkyl groups each having 1 to 32 carbon atoms, wherein $R_2$ is hydrogen and $R_3$ is alkyl, or $R_2$ is alkyl and $R_3$ is hydrogen.

7. The functionalized dendritic polymer of claim 1, wherein F—N is piperazine, $R_2$ is a methyl group, and $R_3$ is a dodecyl group.

8. A coating composition for sorbing and destroying dangerous substances selected from the group consisting of chemical warfare agents, biological warfare agents, toxic industrial chemicals (TICs), and toxic industrial materials (TIMs) comprising functionalized dendritic polymers of Formula I:

$$D_n\text{---}\!\left(R_1\text{---}\!\overset{\oplus}{\underset{\underset{R_2}{|}}{E}}\right)_z \quad X^{\ominus} \quad \text{(Formula I)}$$

wherein:
D is a dendrimer or hyperbranched polymer;
n is the generation number of the dendrimer or the number of branches of the hyperbranched polymer;
z is an integer that is not zero;

X is an anion;
$R_1$ is a linking group;
$R_2$ is hydrogen, alkyl group having 1-32 carbon atoms, an aryl group or chloromethyl; and
E is any nitrogen containing heterocyclic or heteroaromatic ring system of which one nitrogen is covalently bonded to $R_1$ and $R_2$ and has a positive charge, Formula II:

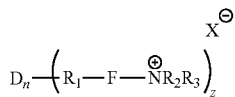
(Formula II)

wherein:
D is a dendrimer or hyperbranched polymer;
n is the generation number of the dendrimer or the number of branches of the hyperbranched polymer;
z is an integer that is not zero;
X is an anion;
$R_1$ is a linking group;
F—N is any nitrogen containing heterocyclic or heteroaromatic ring system in which at least one nitrogen in the ring is quaternized and bonded to $R_2$ and $R_3$ but not to $R_1$;
$R_2$ is a hydrogen, an alkyl group having 1-32 carbon atoms, an aryl group or chloromethyl; and
$R_3$ is a hydrogen, an alkyl group having 1-32 carbon atoms, an aryl group, or chloromethyl,
or a combination thereof.

9. A coated substrate comprising a substrate coated with the coating composition of claim 8.

10. The coated substrate of claim 9, wherein the substrate is a coated polymeric bead, a metal or metal oxide particle, or glass.

11. The coated substrate of claim 9, wherein the substrate is a textile material.

12. The coated substrate of claim 9, wherein the substrate is an air filter.

13. A coating composition for sorbing and destroying dangerous substances selected from the group consisting of chemical warfare agents, biological warfare agents, toxic industrial chemicals (TICs), and toxic industrial materials (TIMs) comprising a quaternary ammonium functionalized dendritic polymer of Formula II:

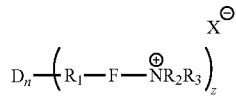
(Formula II)

wherein:
D is a hyperbranched polymer;
n is the number of branches of the hyperbranched polymer;
z is an integer that is not zero;
X is an anion;
$R_1$ is a linking group;
F—N is any nitrogen containing heterocyclic or heteroaromatic ring system in which at least one nitrogen in the ring is quaternized and bonded to $R_2$ and $R_3$ but not to $R_1$;
$R_2$ is a hydrogen, an alkyl group having 1-32 carbon atoms, an aryl group or chloromethyl; and
$R_3$ is a hydrogen, an alkyl group having 1-32 carbon atoms, an aryl group, or chloromethyl, and
wherein D is a poly(ester amide) based hyperbranched polymer.

* * * * *